United States Patent [19]

Nelson et al.

[11] Patent Number: 5,997,530

[45] Date of Patent: Dec. 7, 1999

[54] APPARATUS AND METHOD TO CONTROL ATMOSPHERIC WATER VAPOR COMPOSITION AND CONCENTRATION DURING DYNAMIC COOLING OF BIOLOGICAL TISSUES IN CONJUNCTION WITH LASER IRRADIATIONS

[75] Inventors: J. Stuart Nelson, Laguna Niguel, Calif.; Bahman Anvari, Houston, Tex.; B. Samuel Tanenbaum, Irvine, Calif.; Thomas E. Milner, Austin, Tex.

[73] Assignee: The Regents of the University of California, Oakland, Calif.

[21] Appl. No.: 09/059,537

[22] Filed: Apr. 13, 1998

[51] Int. Cl.$^6$ .................................................. A61B 17/36
[52] U.S. Cl. .................................. 606/9; 606/2; 606/20; 607/80; 607/89
[58] Field of Search ........................... 606/2, 9–11, 13, 606/16, 17, 20, 22; 607/80–84, 88–91

[56] References Cited

U.S. PATENT DOCUMENTS

| 3,749,092 | 7/1973 | Williams | 607/84 |
| 5,300,067 | 4/1994 | Nakajima et al. | 606/16 |
| 5,620,478 | 4/1997 | Eckhouse | 607/88 |
| 5,814,040 | 9/1998 | Nelson et al. | 606/9 |
| 5,824,023 | 10/1998 | Anderson | 607/88 |
| 5,868,732 | 2/1999 | Waldman et al. | 606/9 |

*Primary Examiner*—Linda C. M. Dvorak
*Assistant Examiner*—Bryan Yarnell
*Attorney, Agent, or Firm*—Daniel L. Dawes

[57] ABSTRACT

Cryogen spray cooling of skin surface with millisecond cryogen spurts is an effective method for establishing a controlled temperature distribution in tissue and protecting the epidermis from nonspecific thermal injury during laser mediated dermatological procedures. Control of humidity level, spraying distance and cryogen boiling point is material to the resulting surface temperature. Decreasing the ambient humidity level results in less ice formation on the skin surface without altering the surface temperature during the cryogen spurt. For a particular delivery nozzle, increasing the spraying distance to 85 millimeters lowers the surface temperature. The methodology comprises establishing a controlled humidity level in the theater of operation of the irradiation site of the biological tissues before and/or during the cryogenic spray cooling of the biological tissue. At cold temperatures calibration was achieved by mounting a thermistor on a thermoelectric cooler. The thermal electric cooler was cooled from from 20° C. to about −20° C. while measuring its infrared emission.

20 Claims, 4 Drawing Sheets

APPARATUS AND METHOD TO CONTROL ATMOSPHERIC WATER VAPOR COMPOSITION AND CONCENTRATION DURING DYNAMIC COOLING OF BIOLOGICAL TISSUES IN CONJUNCTION WITH LASER IRRADIATIONS

Part of this invention was made with Government support under grants from the National Science Foundation, BES-9634110, the Whitaker Foundation 96-0235, the Institute of Heart, Lung and Blood 1R154HL58215-01 and the Institute of Arthritis and Musculoskeletal and Skin Disease 1R29-AR41638-01A1, R15-AR43403-01, and IR01-AR42437-01A1 of the National Institutes of Health. This invention was also made with Government support under Grant DE-FG03-91ER61227, awarded by the Department of Energy. The Government has certain rights thereto.

BACKGROUND OF THE INVENTION

1. Field of the Invention

The invention is related to field of laser treatment of biological tissues and in particular to the control of the immediate theater of treatment above and adjacent to the target area of the tissue surface or skin.

2. Description of the Prior Art

Successful laser treatment of hypervascular cutaneous lesions such as port wine stains, hemangiomas and telangiectasias is based on selective photo coagulation of blood vessels by laser heating without inducing thermal injury to the epidermis. Protecting the epidermis from laser induced thermal injury may also be beneficial in treatment of facial rhytides.

One method to overcome non-specific thermal injury is to spray a short cryogen spurt of the order of several milliseconds directly onto the skin's surface immediately prior to laser irradiation as described in the copending applications Ser. No. 08/222,976, filed Apr. 5, 1994, now abandoned, and entitled "Apparatus And Method For Dynamic Cooling Of Biological Tissues For Thermal Mediated Surgery", and Ser. No. 08/870,467, filed on Jun. 6, 1997 and entitled "Method and Apparatus for Causing Spatially Selective Coagulation During Thermally Mediated Procedures," assigned to the same assignee as the present invention and which are incorporated herein by reference. The methodology described therein is hereinafter referenced as cryogen spray cooling.

In contrast to other procedures such as placing ice or a cold substrate such as a cooled sapphire window in contact with the skin, cryogen evaporation on the skin's surface allows a localized cooling of the epidermis without lowering the temperature of the targeted blood vessels. Although preliminary studies indicate that the thermal injury to the epidermis can be reduced or eliminated by cryogen spray cooling while still achieving the therapeutic effect, understanding the cryogen evaporation process both while in transit and at the skin's surface is essential for optimization of the treatment parameters, namely the cryogen physical properties, spurt duration as well as the design of the delivery system.

In particular, what needs to be considered is that the dependence of the radiometric surface temperature of human skin based on: (1) ambient humidity level; (2) spraying distance between the delivery nozzle and the surface; (3) cryogen boiling point; and (4) the geometry of the delivery nozzle or the spray formed by it. Each of these parameters must then be taken into account for devising control of the treatment theater immediately above the skin or in the vicinity of the laser irradiation site to maximize the control of laser treatment combined with cryogen spray cooling.

Water vapor present in the ambient atmosphere during cryogen spray cooling interacts with the cryogen to form ice crystals. Condensation may begin immediately after the cryogen is released from the delivery nozzle into the ambient atmosphere and continues until the cooling capacity of the cryogen is exhausted. Increased water vapor concentration in the ambient atmosphere results in higher rates of condensation. The thermodynamics of the ice crystal formation process is a diversion of the latent heat of evaporation from the relatively short lived liquid cryogen droplets into a cryogen-ice mixture in the solid phase that may exist in the skin surface for hundreds of milliseconds. Additionally, because temperature of liquid cryogen droplets injected from the nozzle into the ambient atmosphere is lower than that of ice crystals, and instantaneous heat flux at the skin surface may be reduced when water vapor is present. Inasmuch as ice crystal formation on tissue surface affects the heat flux, control of water vapor concentration in the ambient environment in the theater of exposure is essential for efficacious or controlled clinical application of cryogen spray cooling.

Therefore, the present invention is a device to control atmospheric water vapor concentration to limit the effects of ice crystal formation on the skin surface during cryogen spray cooling.

BRIEF SUMMARY OF THE INVENTION

The invention is a method for cryogen spray cooling of biological tissue in conjunction with photoradiation comprising the steps of establishing a controlled humidity theater at the site of the irradiation of the biological tissue. In terms of this specification photoradiation is meant to include any type of electromagnetic or other energy field which can be delivered to the biological tissue. In the illustrated embodiment, pulsed or continuous laser energy of any frequency is contemplated. However, the invention expressly contemplates the use of noncoherent light sources such as flashlamps and nonoptical sources such as masers. The site of biological tissue is then cryogenically spray cooled when the humidity of the theater has been established so that thermal mediation of the biological tissue by laser irradiation is controllable and hence repeatable. Cryogenic spray cooling is defined as including the methodologies and apparatus of using droplets a liquid having a boiling point at or below the freezing point of water, usually 0° C.

The step of establishing the controlled humidity theater at the site of irradiation of the biological tissue comprises the step of establishing the controlled humidity within an enclosure which includes the theater. The theater is defined as the minimal area or region in the proximity of the irradiation site beyond which the formation of ice on the tissue surface does not materially affect the thermal mediation of the tissue when cryogenically spray cooled or any larger area or region. The enclosure may or may not include the entire extent of the biological target. For example, the enclosure may be an environmental chamber, or only a hand-held cylinder which includes only the cryogen spray path and the irradiation surface site.

In another embodiment the step of establishing the controlled humidity theater at the irradiation site of the biological tissue comprises the step of flowing a gas having a controlled humidity onto the theater with or without an enclosure of the theater. In particular the gas of controlled humidity is used to flood the theater with the gas, which in the preferred embodiment is a dry gas or dry nitrogen gas.

Thus the step of establishing the controlled humidity of the theater within the enclosure may comprise cryogenically spraying the theater within the enclosure.

The method further comprises the step of measuring humidity within the theater to provide a feedback control signal whereby the controlled humidity theater is established. In the illustrated embodiment a water vapor source and a dry gas source, each of which are coupled to the enclosure, are separately or independently controlled according to the humidity desired and the feedback signal. Generally, to establish a controlled humidity of the theater requires a reduction of the humidity within the theater from ambient humidity levels. Reductions of the humidity in the theater to 5% humidity or less by weight or absolute humidity are practically achievable and provide good results.

In functional terms the humidity is reduced within the theater from ambient humidity to a level sufficient to avoid ice formation on the biological tissue when exposed to the cryogen spray cooling.

The temperature of the surface of the irradiation site is most strongly controlled by controlling the humidity, but it is also controlled in part by varying the distance between the point of injection of the cryogen spray cooling and point of impingement of the cryogen onto the biological tissue within the theater. To a substantially lesser extent the temperature of the surface of the irradiation site is controlled by the boiling point of the cryogen used in the cryogenic spray cooling.

The invention is also an apparatus for cryogen spray cooling biological tissue comprising a source of sprayed cryogen and a humidity level controller for providing a controlled humidity within the theater of laser irradiation of the biological tissue when cryogen is applied thereto from the source. The humidity controller includes a humidity controlled enclosure including an interface open to the theater. Alternatively the controller comprises a source of gas for flooding the theater with a gas having a controlled humidity.

The invention having been briefly summarized above can be better visualized by turning to the following drawings wherein like elements are referenced by the like numerals.

The invention and its various embodiments may now be better administered by turning to the following detailed description.

DETAILED DESCRIPTION OF THE PREFERRED EMBODIMENTS

Cryogen spray cooling of skin surface with millisecond cryogen spurts is an effective method for protecting the epidermis from nonspecific thermal injury during laser mediated dermatological procedures. Control of humidity level, spraying distance and cryogen boiling point is material to the resulting surface temperature. Decreasing the ambient humidity level results in less ice formation on the skin surface without altering the surface temperature during the cryogen spurt. Increasing the spraying distance to 85 millimeters lowers the surface temperature. The methodology comprises establishing a controlled humidity level in the theater of operation of the irradiation site of the biological tissues before and/or during the cryogenic spray cooling of the biological tissue.

Figure 1:
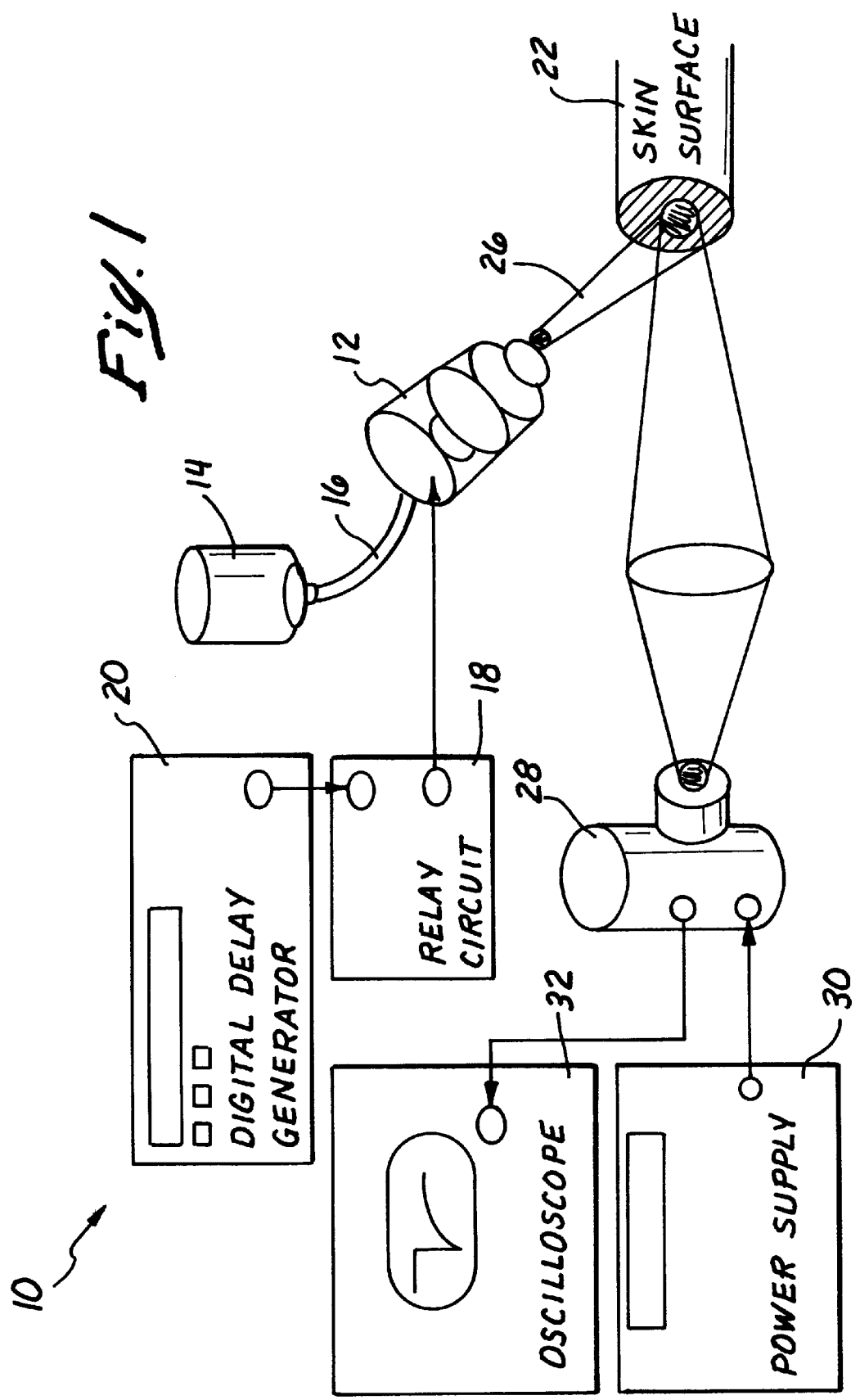
FIG. 1 is a diagrammatic block diagram of a cryogen spray cooling apparatus for cryogen cooling of skin with measurements of radiometric surface temperatures.

FIG. 1 is a diagrammatic depiction of a system, generally denoted by reference numeral 10, for providing cryogenic spray cooling of tissue or skin together with the simultaneous measurement of radiometric surface temperature. Radiometric surface temperature measurements, while beneficial in a therapeutic system 10 may not be necessary and can be omitted if desired. Thus detector 28, power supply 30 and oscilloscope 32 are shown only in the illustrated embodiment as part of a demonstration or test unit in which the effects of the invention are empirically verified. The radiometric surface temperature is measured in the illustrated embodiment of FIG. 1 to provide a demonstration of the operability of the invention.

System 10 is comprised of a cryogen delivery nozzle 12 drawing a supply of cryogen from a reservoir 14. Reservoir 14 is a pressurized steel reservoir which delivers cryogen through a 4 cm long tube 16 having an inner diameter of about 1 mm which is threaded onto the end of an automobile fuel injector 12. Delivery nozzle 12 is controlled by a relay circuit 18 which in turn is controlled by a programmable digital delay generator 20 such as model DG353 manufactured by Stamford Research Systems of Sunnyvale, Calif. In the illustrated embodiment, cryogen spurts in duration of 5–100 ms can be obtained by appropriately inputting the desired timing controls through generator 20. It is to be expressly understood that in any diagnostic or therapeutic system 10 the control of delivery nozzle 12 may be provided by an entirely different circuit and instead of an automobile fuel injector, other more specialized cryogenic injectors can be equivalently substituted. For example, specialized cryogen injectors can be devised in which cryogen reservoir 14 is integrally combined with delivery nozzle 12 together with onboard electronics so that the entire unit is hand held and self-contained. The arrangement of system 10 shown in FIG. 1 is a bench-top experimental prototype and the commercialized version may be implemented in a different way without departing from underlying concepts illustrated here.

In addition, it must be understood that in a diagnostic or therapeutic device, typically delivery nozzle 12, will be combined with a pulse or continuous wave light source, e.g. laser (not shown), which provides the thermal mediation to the biological target which in this case is human skin 22 having surface 24 upon which cryogen spray 28 impinges. The laser beam will be similarly directed or focused onto surface 24 so that both the thermal mediation through laser heating as well as dynamic cooling through cryogen spray or spurt 36 may be delivered by the same assembled unit either in sequence or simultaneous. The laser, its power supply and control electronics has been omitted from the depiction FIG. 1 for the purposes of simplicity, but it must be understood that the invention is to be used in combination with a conventional laser or optical source of energy.

In the following description, the exposures are performed inside a visibly transparent chamber shown in FIG. 5 of approximately 85 by 50 by 40 cm in which controlled ambient humidity levels are established. Thus, the entire theater of operation in which skin surface 24 is exposed is at a humidity level as described below. Controlled ambient humidity levels are obtained by flushing the environmental or containment chamber 62 with dry nitrogen gas. An electrical hygrometer, such as model RH411 manufactured by Omega Engineering of Stamford, Conn., is placed inside exposure chamber 62 to measure the humidity level. A live human volunteer placed his or her forearm inside the chamber for exposure through an opening 74 in the sidewall of chamber 62 which is sealed with a neoprene gasket, which forearm is symbolically represented by tissue target 22 with skin surface 24 in FIG. 1.

A single element, liquid nitrogen cooled infrared HgCdTe detector 28, such as Model MDD-10E0-S1 manufactured by Cincinnati Electronics of Mason, Ohio is mounted on a three axis micropositioner positioned (not shown) inside environmental chamber 62 to measure the skin radiometric surface temperature. Detector 28 is optically filtered at the cold stop with a 10.6–14 micron bandpass filter. Infrared detector 28 is calibrated by measuring the output voltage of detector 28 as a function of the surface temperature of a copper block standard (not shown) coated with highly admissive black paint. The copper block is heated by resistive elements from 23 to 70° C. while measuring the surface temperature with a precision thermistor such as Model 8681 manufactured by Keithley Instruments of Cleveland, Ohio. Detector 28 is calibrated before each set of exposures discussed below.

Skin surface sites 24 and the fingers of volunteers are sprayed with cryogen and the radiometric surface temperature measured while varying the humidity level, spraying distance in the cryogen is set forth in Table 1 below. All cryogens are nontoxic and environmentally compatible replacements for chlorofluorocarbons. Exposures are conducted with humidity levels in the chamber set at 60%, 30% and 5% by weight and at spraying distances between 8 to 100 mm, which is the distance between the tip of delivery nozzle 12 and target surface 24 as will be described in greater detail in connection with FIGS. 2, 3, 4a and 4b.

The cryogens used are summarized in Table 1 below:

TABLE 1

| Cryogen | composition by weight | boiling point ° C. at 1 atmosphere |
|---|---|---|
| R134A | 100% tetrafluoroethane | −26 |
| R407C | 54% tetrafluoroethane<br>25% pentafluoroethane<br>23% difluoromethane | −43 |
| R404A | 4% tetrafluoroethane<br>44% pentafluoroethane<br>52% trifluoroethane | −48 |

Figure 2:
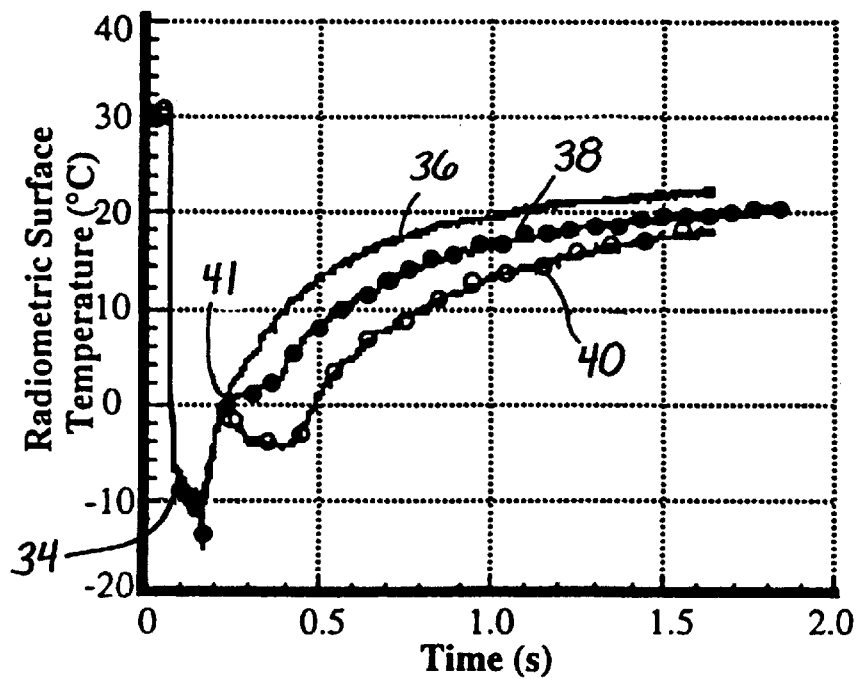
FIG. 2 is a graph of the radiometric surface temperature of the skin as a function of time based on various humidity levels in the theater of the laser irradiation site.

Inasmuch as water vapor present in air undergoes condensation under interaction with cryogen droplets to form ice, which is subsequently deposited on skin surface 24, the effects of ambient humidity levels are examined during cryogenic spray cooling. Radiometric surface temperatures during the cryogenic spurt is not affected when reducing the ambient humidity level to a minimum of 5% as shown in FIG. 2. FIG. 2 is a graph of the radiometric surface temperature (°C.) as a function of time in seconds. Increasing the humidity level resulted in more ice formation on the skin surface as evidenced by the quasi-equilibrium state corresponding to a phase transition. Distinct temperatures at which phase transition occurred are noted below.

For example, in FIG. 2, which is graph of the radiometric surface temperature versus time for 5%, 30% or 60% humidity levels as shown by curves 36, 38 and 40 respectively at a spraying distance fixed at 60 mm using a cryogen spurt of R-134A cryogen of 80 milliseconds, two phase transitions 41 occur at 0° C. which correspond to the melting of ice and at approximately −6° C. at 34 which may be due to melting of a binary mixture of liquid cryogen and ice. As clearly shown in FIG. 2, the skin surface temperature is affected by varying levels of humidity with the temperature reaching lower levels and remaining cooler for longer periods of time with increasing humidity. Temperature differences according to humidity become dramatic at about 0.4 seconds and thereafter.

Figure 3:
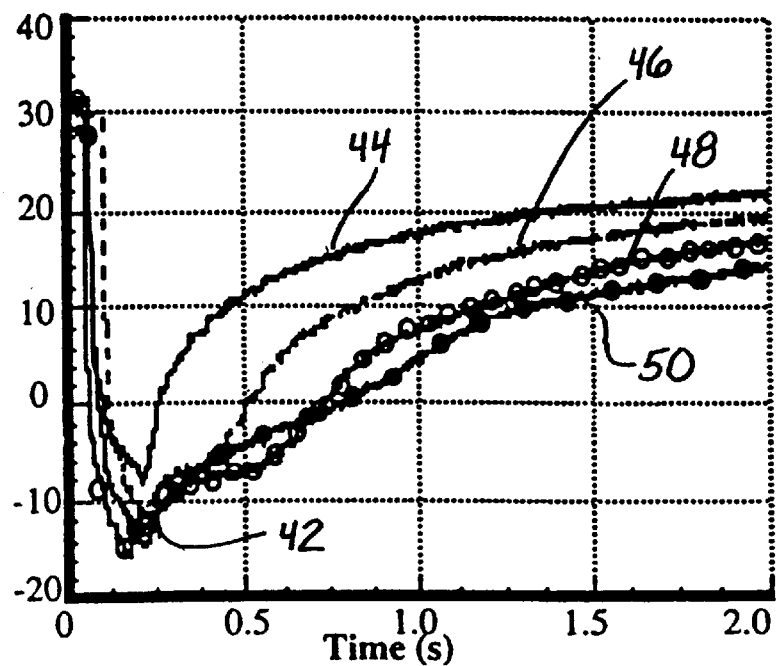
FIG. 3 is a graph of the radiometric surface temperature as plotted against time showing the dependence upon the spraying distance.

The dependence of skin radiometric surface temperature upon the spraying distance between the nozzle and the skin is graphically illustrated in FIG. 3 in which temperature in ° C. as a function time in seconds is shown for spraying distances of 8, 50, 85 and 100 mm by curves 44, 46, 48 and 50 respectively using cryogen R-134A at a constant humidity level of 60% with a 50 ms cryogen spurt. Increasing spraying distance from 8 to 85 mm resulted in the reduction of radiometric temperature by an additional 10° C. during the spurt. Increased distance may allow sufficient time for the core of droplets to cool substantially before striking the skin surface as the outer layers of the droplets evaporate in flight. Additional reduction of the skin radiometric surface temperature is not achieved with increasing spraying distance up to 100 mm.

At short spraying distances of less than about 35 mm, no ice formation is observed. This is confirmed by visual inspection of the skin surface and absence of a quasi-equilibrium state in the recorded radiometric signal. A phase transition is observed at approximately −9° C. at 42 in FIG. 3 for spraying distances of 85 and 100 mm.

Figure 4A:
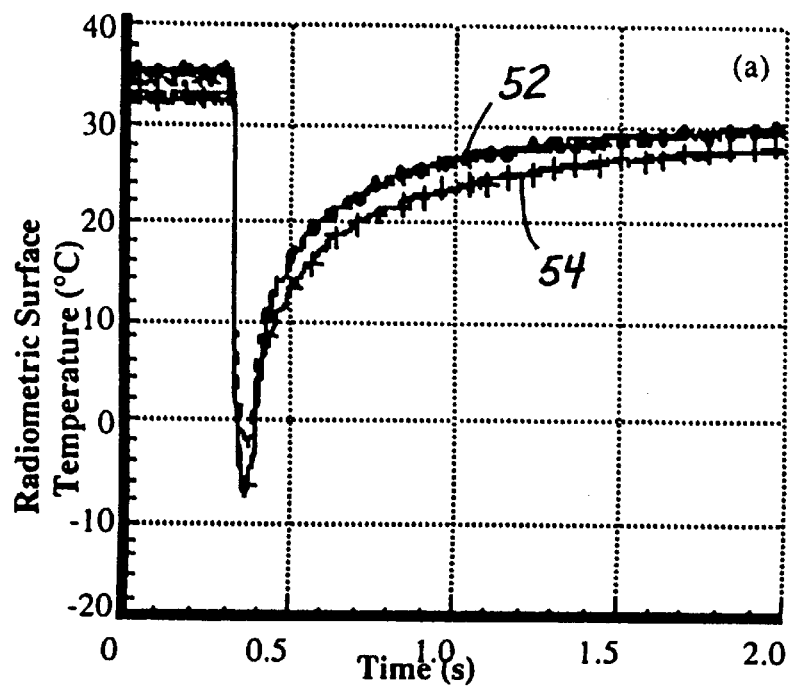
FIG. 4A is a graph showing the radiometric surface temperature's function time illustrating the effect of cryogen boiling point for a first spraying distance of 8 mm.

Consider now the effect of cryogen boiling point as shown in FIGS. 4a and b. In general, the boiling point of the cryogen used did not have a considerable effect on the radiometric surface temperature of the skin. FIGS. 4a and b are graphs of radiometric surface temperature in ° C. verses time in seconds. For relatively short spraying distance of 8 mm as shown in FIG. 4a, only an additional 5° C. radiometric surface temperature reduction is obtained when spraying the skin with cryogen R-407C or R-404A instead of R-134A as shown in FIG. 4A with boiling point differences of −43° C. −48° C. and −26° C., respectively as shown by the differences in curves 52 and 54.

Figure 4B:
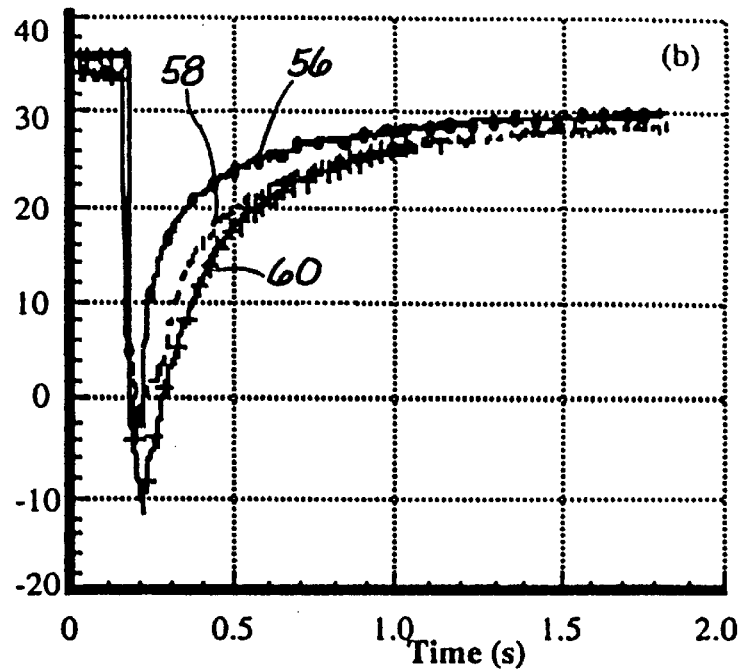
FIG. 4B is a graph of the radiometric surface temperature versus time similar to FIG. 4A showing the effect of cryogen boiling point on the radiometric surface temperature for a spraying distance of 80 mm.

For a relatively long spraying distance of 80 mm as shown in FIG. 4b, lower radiometric surface temperatures are obtained when spraying the skin with R-407C in curve 60, one of the cholorcryogens, whereas R-404A and R-134A realized higher temperatures as shown by curves 56 and 58 respectively. Regardless of the spraying distance, ice formation is minimal or absent with cryogen R-404A and further reduction to surface temperatures are not achieved.

Based on the foregoing, it is clear that altering the ambient humidity level does not change the resulting radiometric surface temperature during a cryogen spurt. However, the amount of ice formation is clearly affected. It is believed that ice formation introduces an uncontrollable parameter in the thermal exposure of the tissue and may not be clinically desirable. The thermal profile of the laser radiation site can materially affect the success or failure of the treatment depending upon the application question. Increasing the spraying distance resulted in lowered radiometric surface temperatures and more ice formation when using the lower temperature cryogens. Additional radiometric surface temperature reductions are not achieved by changing cryogens used in these experiments.

Therefore, according to the invention, effective ice crystal formations on the skin surface during cryogen spray cooling in conjunction with laser radiation is achieved by controlling the atmospheric composition, the environment or theater of the exposure, the concentration of water vapor and other gases.

Figure 5:
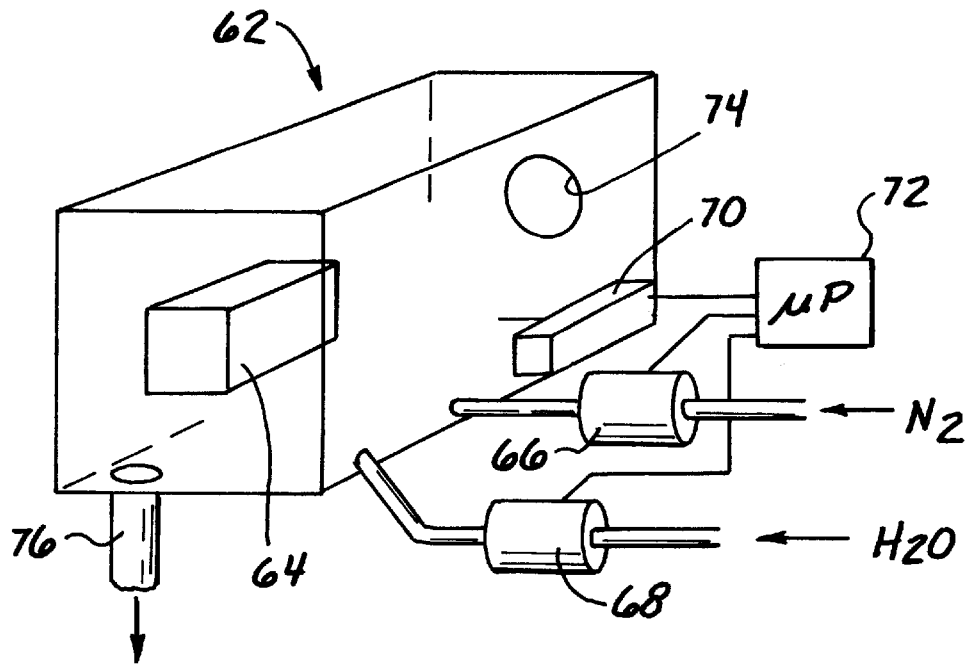
FIG. 5 is a diagrammatic depiction of an apparatus wherein the humidity is controlled in the vicinity of the cryogen spray cooling and the irradiation site on the tissue using a closed chamber.

FIG. 5 diagrammaticly depicts a sealed transparent enclosure, generally denoted by reference numeral 62. Enclosure 62 contains the cryogen spray cooling elements 12, 14, 18 and 20 described in connection with FIG. 1 which are collectively and diagrammaticly depicted in FIG. 5 by reference numeral 64. An electrically controlled solenoid valve 66 is coupled to a source of dry nitrogen while a similar electrically controlled solenoid valve 68 is coupled to a source of water vapor. A feedback system, generally denoted by reference numeral 70, including an electronic hygrometer is coupled to a data acquisition and computer controller 72, which also are coupled to and controlled solenoid valves 66 and 68 to maintain atmospheric water vapor concentration with enclosure 62 at a desired level. A one-way vent valve 76 is provided to enclosure 62 to allow gaseous flushing of enclosure 62 until the desired humidity concentration is obtained.

Cryogen and/or laser radiation is directed from cryogen spray cooling unit 64 to a target window 74 within enclosure 62 placed over skin surface 24 or alternatively through which the biological target is inserted with a temporary moisture seal. Alternatively, the laser (not shown) can be mounted exteriorly to enclosure 62 and focused through it onto target window 74.

Figure 6:
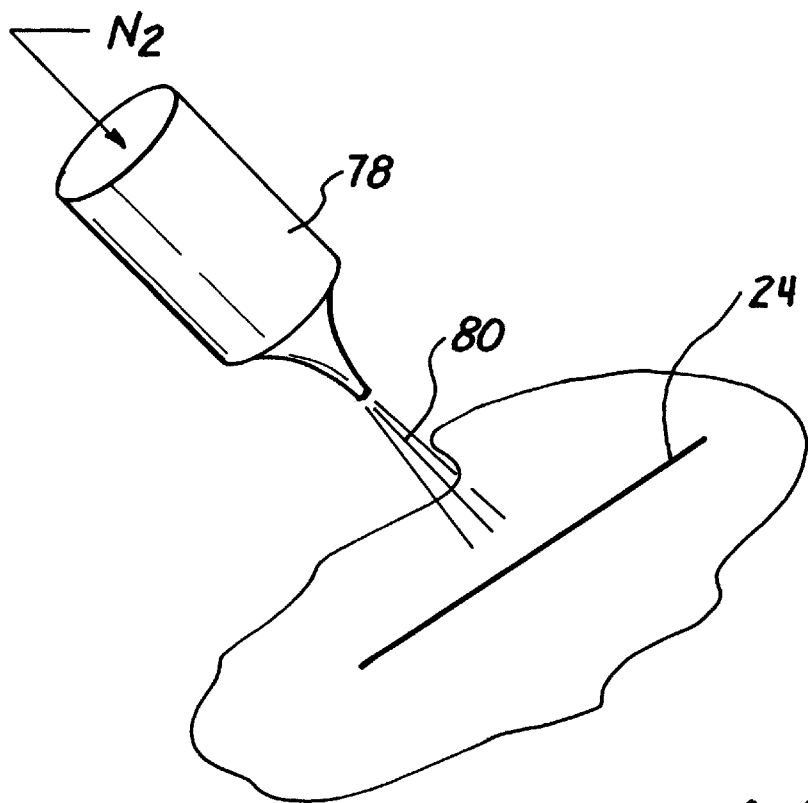
FIG. 6 is a diagrammatic depiction of another embodiment of the apparatus wherein humidity is controlled in the vicinity of the cryogen spray cooling and the irradiation site on the tissue using a gas jet to flood the theater.

In another embodiment such as diagrammaticly shown in FIG. 6 a cryogen spray cooling device 78 including all or part of components 12, 14, 16, 18 and 20 on FIG. 1 is focused onto target surface 24 and is provided with a dry nitrogen spray or jet 80 which can be selectively turned on for a predetermined time prior to exposure to flood the immediate environment or theater of irradiation with dry nitrogen followed by or simultaneously with the application of the cryogen spray cooling and/or laser radiation of surface 24. Therefore, while no enclosure of the operating theater is provided, the ambient air is temporarily removed from the irradiation site at surface 24 by flooding the theater operation and the cryogen spray path with a dry or a controlled humidity cloud of gas. In this way when the cryogen is applied, ice formation is prohibited or at least substantially reduced thereby avoiding interference with the thermal affects of the laser radiation.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for cryogen spray cooling of biological tissue in conjunction with photoradiation comprising:
   providing a laser;
   establishing a controlled humidity theater at a site of irradiation of said biological tissue; and
   cryogenically spray cooling said site of biological tissue when the humidity of said theater has been established so that thermal mediation of said biological tissue by laser irradiation is controllable and hence repeatable.

2. The method of claim 1 where establishing said controlled humidity theater at said site of irradiation of said biological tissue comprises establishing said controlled humidity within an enclosure which includes said theater.

3. The method of claim 2 where establishing said controlled humidity of said theater within said enclosure further comprises cryogenically spraying said theater within said enclosure.

4. The method of claim 2 further comprising controlling the temperature of a surface of said site of irradiation according to a distance between a point of injection of said cryogen spray cooling and a point of impingement of said cryogen onto said biological tissue within said theater.

5. The method of claim 1 wherein establishing said controlled humidity theater at said irradiation site of said biological tissue comprises flowing a gas having a controlled humidity onto said theater without an enclosure of said theater.

6. The method of claim 5 where flowing said gas having said controlled humidity comprises flooding said theater with said gas.

7. The method of claim 6 where flooding said theater with said gas comprises flooding said theater with a dry gas.

8. The method of claim 7 where flooding said theater with dry gas comprises flooding said theater with dry nitrogen gas.

9. The method of claim 5 further comprising controlling the temperature of a surface of said site of irradiation according to a distance between a point of injection of said cryogen spray cooling and a point of impingement of said cryogen onto said biological tissue within said theater.

10. The method of claim 1 where establishing said controlled humidity theater at said site of irradiation of said biological tissue comprises establishing said controlled humidity within an enclosure which includes said theater and further comprising measuring humidity within said theater to provide a feedback control signal whereby said controlled humidity theater is established.

11. The method of claim 10 where establishing said controlled humidity of said theater within said enclosure further comprises cryogenically spraying said theater within said enclosure.

12. The method of claim 11 wherein establishing humidity control within said enclosure according to said feedback signal comprises separately controlling a water vapor source and a dry gas source, each source being coupled to said enclosure.

13. The method of claim 1 wherein establishing said controlled humidity of said theater comprises reducing said humidity within said theater from ambient humidity.

14. The method of claim 13 wherein reducing said humidity within said theater from ambient humidity reduces said humidity to a level sufficient to avoid ice formation on said biological tissue when exposed to said cryogen spray cooling.

15. The method of claim 14 further comprising controlling the temperature of a surface of said site of irradiation by choice of the boiling point of the cryogen used in said cryogenic spray cooling.

16. The method of claim 14 further comprising controlling the temperature of a surface of said site of irradiation according to a distance between a point of release of said cryogen spray cooling and a point of impingement of said cryogen onto said biological tissue within said theater.

17. The method of claim 1 wherein reducing said humidity within said theater from ambient humidity reduces said humidity in said theater to 5% humidity or less by weight.

18. An apparatus for cryogen spray cooling biological tissue comprising:

a laser;

a source of sprayed cryogen; and means for providing controlled humidity within a theater of laser irradiation of said biological tissue when cryogen is applied thereto from said source.

19. The apparatus of claim 18 wherein said means comprises a humidity controlled enclosure including at least as an interface thereof at said theater.

20. The apparatus of claim 18 wherein said means comprises means for flooding said theater with gas having a controlled humidity.

* * * * *